United States Patent [19]
Fuhrman et al.

[11] Patent Number: 5,643,215
[45] Date of Patent: Jul. 1, 1997

[54] GAS EXCHANGE APPARATUS AND METHOD

[75] Inventors: Bradley P. Fuhrman; Mark S. Dowhy; Lynn J. Hernan, all of Buffalo, N.Y.

[73] Assignee: The Research Foundation of State University of New York, Albany, N.Y.

[21] Appl. No.: 393,780

[22] Filed: Feb. 24, 1995

[51] Int. Cl.$^6$ .................................................. A61B 19/00
[52] U.S. Cl. .............................. 604/151; 604/4; 604/131; 600/16
[58] Field of Search ................................ 604/4, 131, 151; 600/16; 415/63, 900; 417/356, 417; 261/DIG. 28

[56] References Cited

U.S. PATENT DOCUMENTS

| | | | |
|---|---|---|---|
| 4,625,712 | 12/1986 | Wampler | 128/1 D |
| 4,753,221 | 6/1988 | Kensey et al. | 415/900 X |
| 4,779,614 | 10/1988 | Moise | 600/16 |
| 4,817,586 | 4/1989 | Wampler | 604/151 X |
| 4,846,152 | 7/1989 | Wampler et al. | 604/151 X |
| 4,908,012 | 3/1990 | Moise et al. | 604/151 X |
| 4,919,647 | 4/1990 | Nash | 415/900 X |
| 4,957,504 | 9/1990 | Chardack | 415/356 X |
| 4,969,865 | 11/1990 | Hwang et al. | 600/16 |
| 4,994,722 | 7/1990 | Carricker et al. | 600/16 |
| 5,040,944 | 8/1991 | Cook | 415/72 |
| 5,092,844 | 3/1992 | Schwartz et al. | 604/151 |
| 5,112,200 | 5/1992 | Isaacson et al. | 604/151 X |
| 5,112,292 | 5/1992 | Hwang et al. | 600/16 |
| 5,211,546 | 5/1993 | Isaacson et al. | 417/356 |
| 5,290,236 | 3/1994 | Mathewson | 604/131 X |
| 5,501,574 | 3/1996 | Raible | 415/900 X |

FOREIGN PATENT DOCUMENTS

WO92/19300  11/1992  WIPO.

OTHER PUBLICATIONS

Fuhrman et al., *Pediatric Critical Care*, 1992, pp. 545–557.
Prough et al., *Critical Care, State of the Art*, 1993, pp. 221–237.

Primary Examiner—Sam Rimell
Attorney, Agent, or Firm—Heslin & Rothenberg, P.C.

[57] ABSTRACT

The invention comprises the use of helical propellers as pumping mechanisms, in various sizes and configurations, to improve upon present devices involving the circulation of liquid solutions between gas exchange mechanisms and subjects to which the liquid solutions are delivered. These improvements include the use of helical propellers as the primary source of fluid propulsion within the system, the use of helical propellers for supplementary fluid propulsion at points of high resistance or low pressure, and the use of reversible-flow helical propellers to achieve bi-directional variable rate flow through single lumen conduits.

15 Claims, 13 Drawing Sheets

GAS EXCHANGE APPARATUS AND METHOD

BACKGROUND OF THE INVENTION

The invention pertains to systems for circulation of a liquid solution between a gas exchange apparatus and a subject to which the liquid solution is being supplied.

One such system is used for extracorporeal membrane oxygenation (ECMO) or cardiopulmonary bypass, in which venous blood is circulated through an extracorporeal oxygenation system and returned to the subject's circulatory system. Venous blood received through a venous cannula is transported past a saturation monitor to a bladder reservoir. The reservoir feeds a pump which drives the blood through a membrane oxygenator and heat exchanger, returning it finally to the subject's circulatory system through an output cannula. A bridge circuit may be opened to allow circulation of blood within the oxygenation system to bypass the subject's circulatory system to prevent a pressure buildup in the oxygenation branch of the ECMO circuit or to create a flow through the oxygenator which is greater than the flow to the patient.

Two forms of ECMO are currently in use. In venoarterial ECMO, the output conduit of the oxygenation system empties into an artery through an arterial cannula, placed typically in the carotid artery. In venovenous ECMO, the output conduit empties into the patient's venous circulation, typically through a cannula in the femoral vein, jugular vein, or right atrium.

An inherent limitation of all ECMO systems is that the rate of oxygenation depends on the flow of venous blood into the oxygenation system. This flow results primarily from circulatory pressure, and is limited by the impedance of the venous cannula. ECMO systems are further limited by their pumping means. The roller pumps and centrifugal pumps which are presently employed are adequate to provide continuous circulation, but cannot provide pulsatile flow. Roller pumps have the additional disadvantage of not allowing "slip" in the event of pressure buildup in the oxygenation branch of the ECMO circuit.

A disadvantage particular to renovenous ECMO is that a portion of the oxygenated blood provided to the subject is taken up again by the venous intake cannula before the blood can be circulated through the subject's circulatory system. This decreases systemic oxygen delivery and reduces the driving pressure (oxygen pressure drop) across the oxygenation membrane, thereby decreasing the efficiency of ECMO. Another disadvantage of venovenous ECMO is that cannulation of the femoral vein with a sufficiently large cannula has proven difficult in infants. While some success has been achieved using a double lumen cannula placed into the jugular vein, the use of the double lumen cannula may increase the wasteful recirculation of oxygenated blood through the oxygenation circuit and greatly reduces the potential diameter of each lumen.

A second apparatus for circulation of a liquid solution between a gas exchange apparatus and a subject is used in tidal liquid ventilation (TLV). TLV uses a liquid solvent such as a perfluorocarbon as a medium for the exchange of oxygen and carbon dioxide within a patient's lungs. A volume of oxygenated solvent is propelled through an endotracheal tube into the subject's lungs. The liquid expands the lungs, which subsequently recoil and expel the oxygen-depleted solvent back through the endotracheal tube and into the TLV circuit. The solvent is then reoxygenated and recirculated.

A disadvantage of present TLV systems is that they lack fine control of the flow rate during inspiration and expiration. A second disadvantage is that they cannot accommodate the long term need for slip. Present systems are only capable of providing a predetermined volume of fluid, and cannot compensate when this volume exceeds the patient's lung capacity.

SUMMARY OF THE INVENTION

The invention comprises the use of helical propellers as pumping mechanisms, in various sizes and configurations, to improve upon present devices involving the circulation of liquid solutions between gas exchange mechanisms and bodies to which the liquid solutions are delivered. These improvements include the use of helical propellers as the primary source of fluid propulsion within the system, the use of helical propellers for supplementary fluid propulsion at points of high resistance or low pressure, and the use of reversible-flow helical propellers to achieve hi-directional variable rate flow through single lumen conduits.

DETAILED DESCRIPTION OF INVENTION

I Helical Propeller as Primary Source of Fluid Propulsion in ECMO

Figure 1:
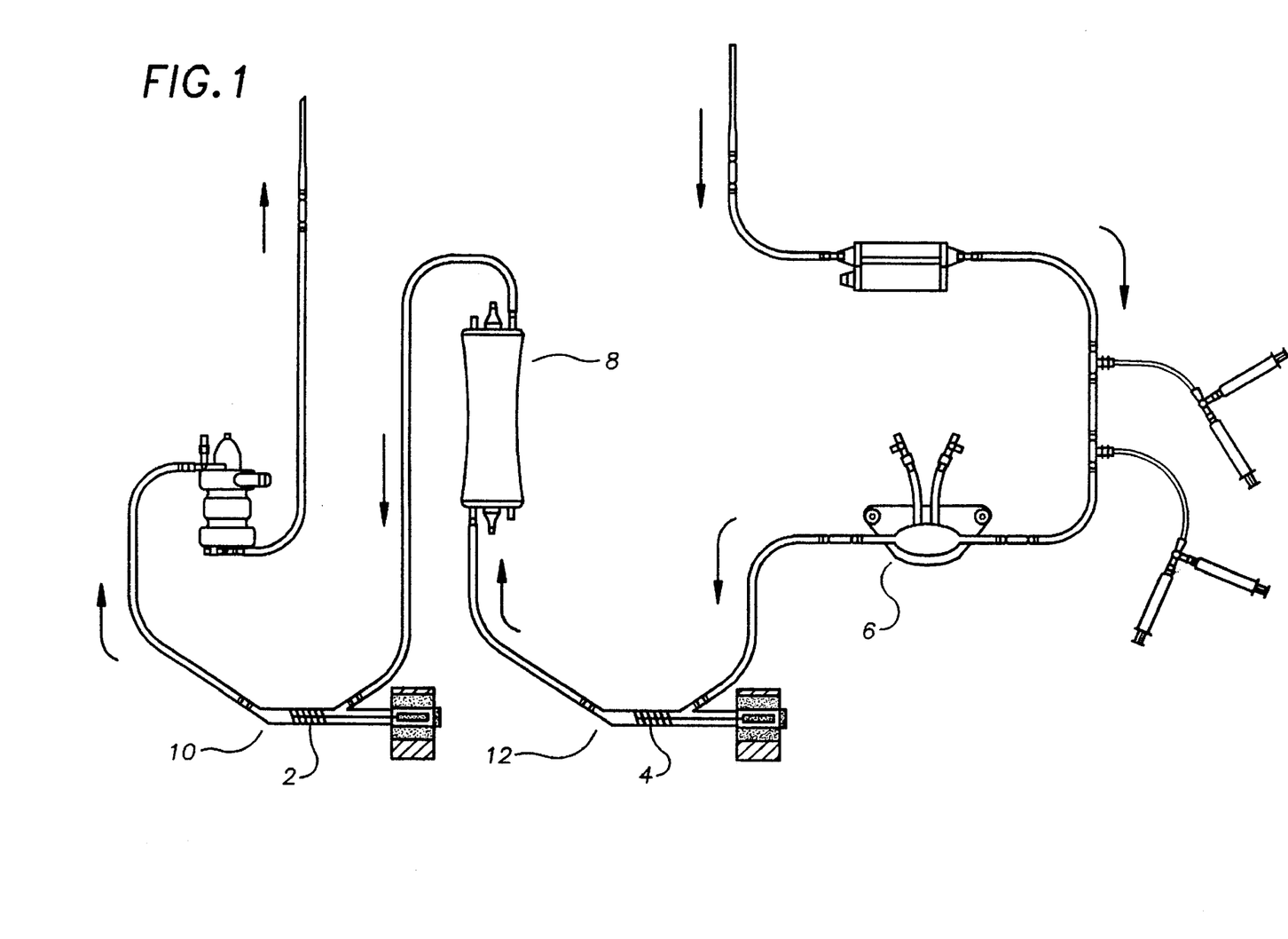
FIG. 1: A venoarterial ECMO circuit driven by helical propellers.

FIG. 1 shows a venoarterial ECMO system in which fluid propulsion is supplied primarily by two helical propellers 2 and 4 disposed within two propulsion units 10 and 12 which are in fluid communication with the lumen of the ECMO circuit. The first propeller 4 supplies pressure which augments the pressure of the venous blood emptying from the bladder reservoir 6 of the ECMO system, and drives this fluid through the membrane oxygenator 8. The second propeller 2 supplies additional fluid pressure to compensate for any damping caused by the impedance of the membrane oxygenator 8. The rotational speed of the pumps and the pitch of the propellers may be selected to accommodate differences in impedance between the oxygenator and the patient's circulatory system.

Figure 2:
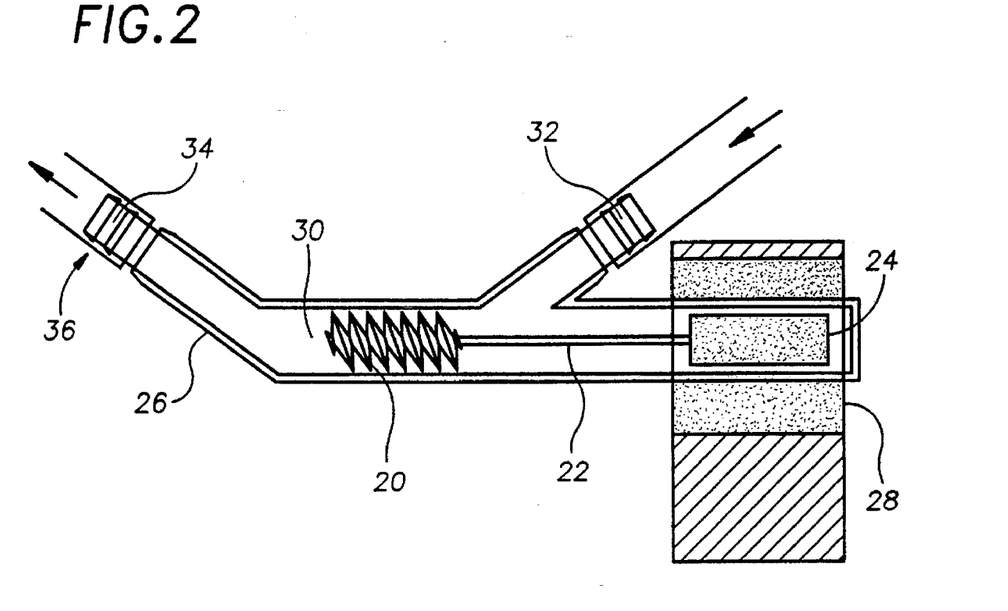
FIG. 2: An ECMO propulsion unit driven by a coil and magnet.

The propellers in each propulsion unit are constructed of a material which is ideally rigid, nonthrombogenic, nonhemolytic, and bioinert, and are caused to rotate by an associated driving mechanism which is integral with the propulsion unit. FIG. 2 shows the preferred configuration for a propulsion unit as utilized in the ECMO system of FIG. 1. A helical propeller 20, drive shaft 22, and magnet 24 are disposed within a propulsion unit casing 26. The casing 26 is composed of a material which is ideally translucent or transparent, rigid, nonthrombogenic, nonhemolytic, and bioinert. The helical propeller 20 is caused to rotate by the drive shaft 22, which is affixed coaxially thereto at one end. At its opposite end, the shaft is joined coaxially to a magnetic cylinder 24. The magnetic cylinder 24 is caused to rotate when electrical current is applied by means of electrical contacts (not shown) to a coil of wire 28 which is disposed about the magnetic cylinder and external to the casing. The rotation of the magnetic cylinder imparts rotation to the drive shaft, and so to the helical propeller.

The propulsion unit casing 26 is shaped such that it defines a lumen 30 within which the helical propeller, drive shaft, and cylindrical magnet can freely rotate. The casing further defines an input port 32 and an output port 34 to which the flexible tubing of the ECMO system (shown attached) may be adjoined. The ports are cylindrical and are provided on their outer surfaces with a plurality of annular ribs 36. The ribs serve to engage the wall of the lumen of the flexible tubing and thereby retain its connection to the propulsion unit.

Figure 3:
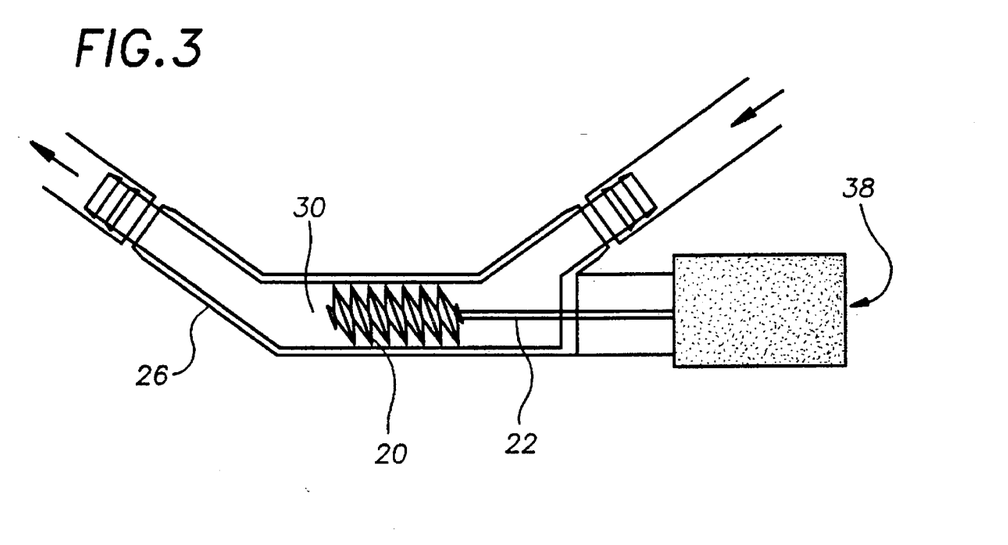
FIG. 3: An alternative ECMO propulsion unit driven by an electric motor.

FIG. 3 shows an alternative configuration of a propulsion unit incorporating a helical propeller. This embodiment differs from the previous one in that the drive shaft extends through a sealed aperture in the casing to an electrical motor 38 which is disposed externally to the casing.

Figure 4:
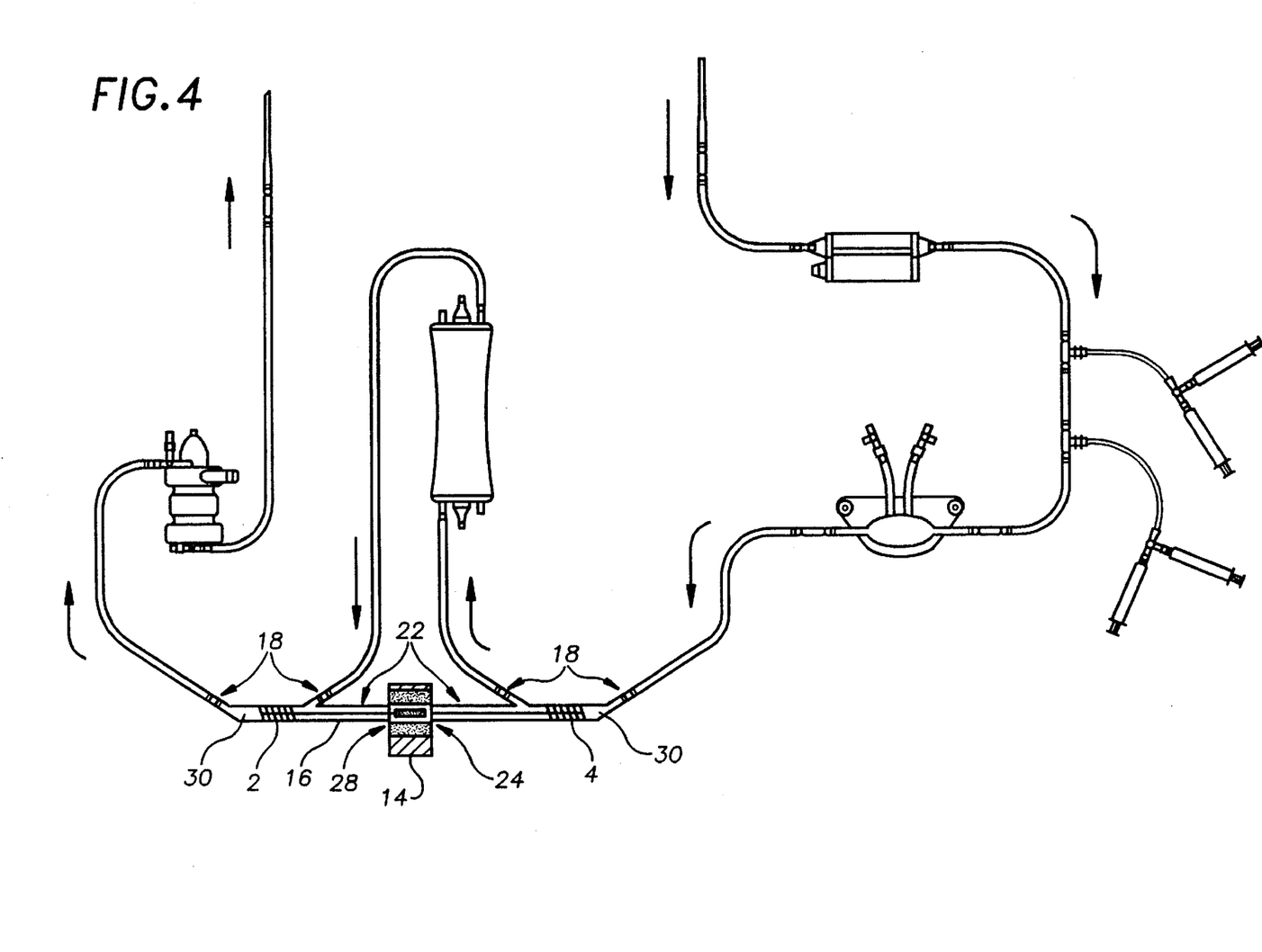
FIG. 4: A venoarterial ECMO circuit driven by an alternative propulsion unit.
Figure 5:
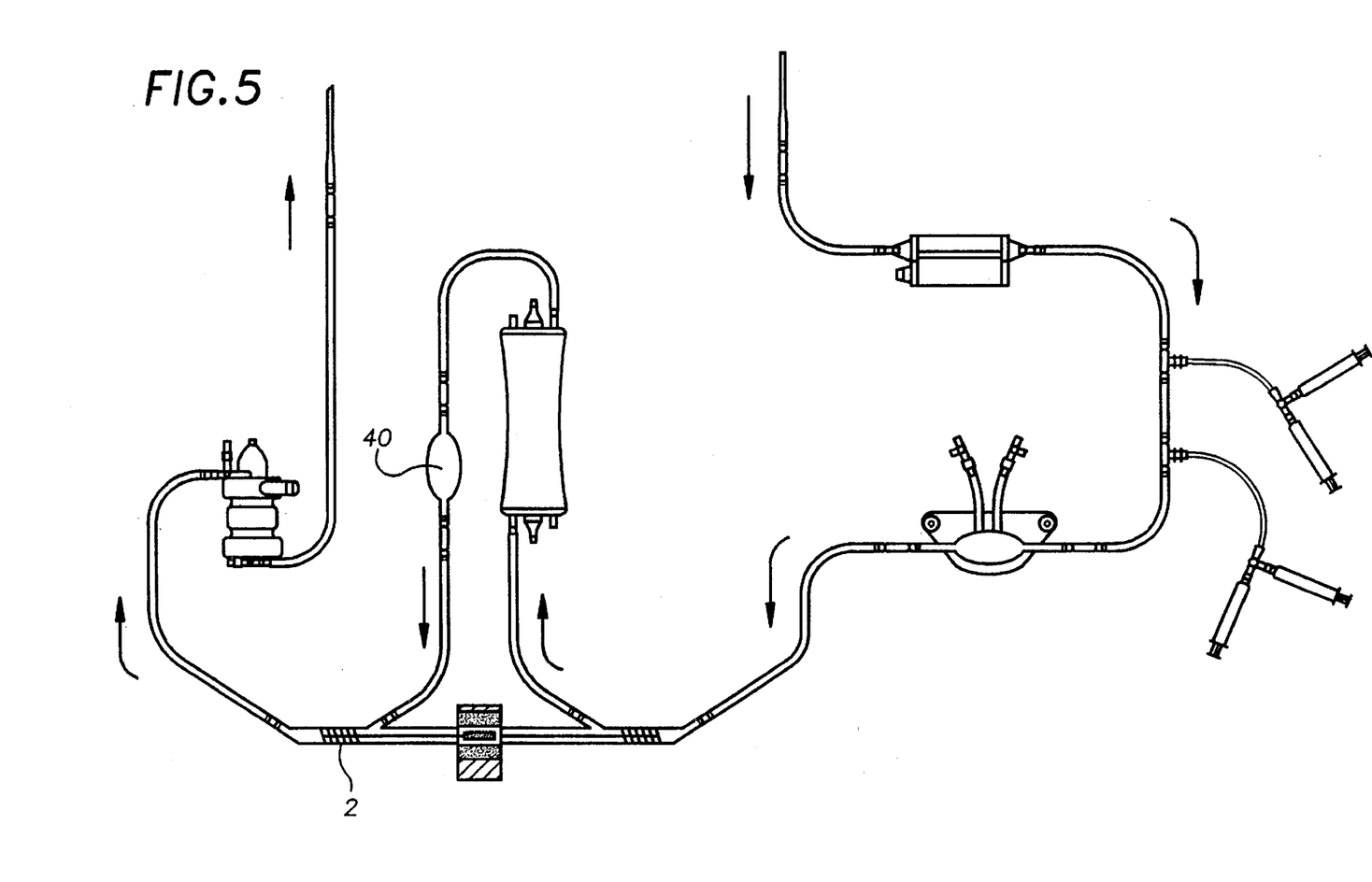
FIG. 5: A venoarterial ECMO circuit including a compliant reservoir for oxygenated blood.

An alternative embodiment utilizing two helical propellers 2 and 4 driven by a single driving means 14 is shown in FIG. 4. In this embodiment, a single casing 16 houses a dual propulsion unit comprising two helical propellers 2 and 4 and two drive shafts 22 which are united by a single cylindrical magnet 24. A coil 28 disposed about the cylindrical magnet 24 and external to the casing serves to turn the propellers in unison upon the application of an electrical current to the coil. The propulsion unit casing shown in FIG. 4 defines two sets of input and output ports 18 and two lumens 30 through which fluid flow is induced. A common electrical motor, with attendant sealing mechanisms, could be substituted in the manner of the first alternative embodiment described above. As in the embodiment described above, propeller pitch can be selected to accommodate impedance differences and to foster output matching. The short response time of a helical propeller system to changes in the rate of rotation of the propeller facilitates the generation of pulsatile flow through the ECMO system. Pulsatile flow is achieved by the application to the electrical coil of an electrical current which corresponds in amplitude over time to the desired pressure waveform. In an embodiment using the separate propulsion units of FIG. 1, only the corporeal branch of the ECMO circuit need be driven with pulsatile current to create pulsatile flow. Pulsatile flow may also be achieved using the unified propulsion units of FIG. 4. In either embodiment, a compliant reservoir, as shown in FIG. 5, may be disposed between the membrane oxygenator and the second helical propeller to compensate for damping of pulsatile flow to the body caused by the time constant of the membrane oxygenator and the pre-oxygenation segment of the ECMO circuit.

II. Helical Propeller as Supplementary Source of Fluid Propulsion in ECMO

Typical ECMO circuits are supplied with a continuous flow of venous blood which is driven by a pump located at the approximate midpoint of the circuit, as in the embodiments described above. Pump output volume is limited by the volume of venous blood which is supplied to the input branch of the ECMO circuit. Flow to the pump has heretofore been passive, driven by intravascular pressure and supplemented by gravity and the negative pressure generated by the pump. This flow is impeded by the narrowness of the lumen of the cannula which receives venous blood and by the length of the cannula.

Figure 6:
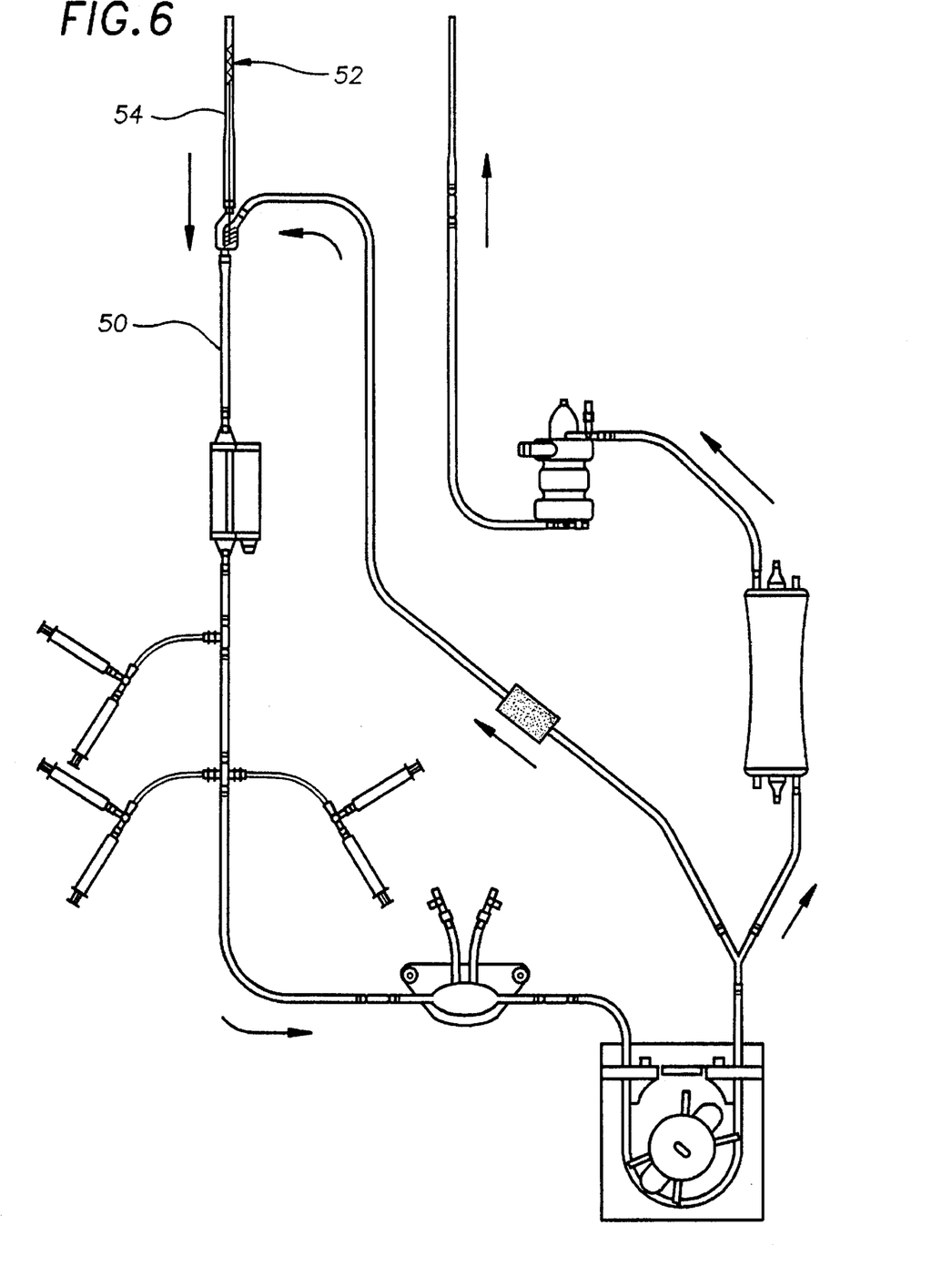
FIG. 6: A venoarterial ECMO circuit including an active pumping cannula.

FIG. 6 shows a typical venoarterial ECMO circuit in which venous blood flow to the input branch 50 of the circuit is assisted by a helical propeller 52 rotating within the venous cannula 54. The propeller serves to actively draw venous blood into the venous cannula and to propel this blood forward through the ECMO circuit to the primary pumping mechanism.

Figure 7:
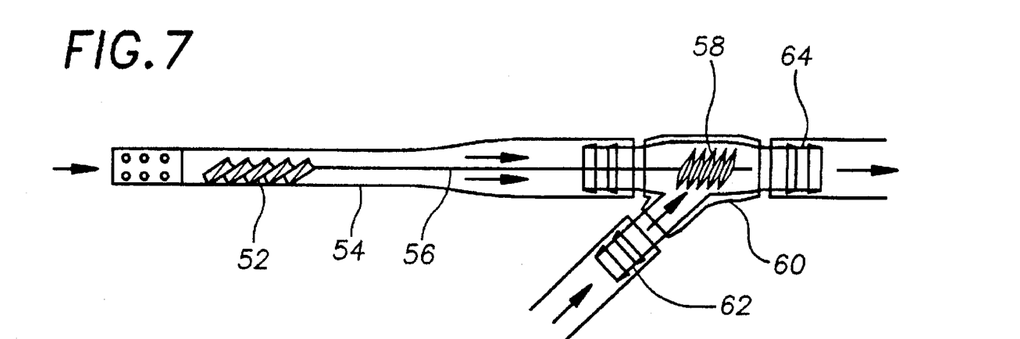
FIG. 7: An active pumping cannula.

FIG. 7 shows one embodiment of an active pumping cannula. In this embodiment, a helical propeller 52 disposed within the venous cannula 54 is joined coaxially to a drive shaft 56. At its opposite end, the drive shaft 56 is joined coaxially to a helical driver 58 which is located within a casing 60 and which is caused to rotate by the flow of fluid entering the input branch of the ECMO circuit from the bridge circuit through an input port 62. Venous blood and bridge circuit blood empty from the cannula through an output port 64 and into the input branch of the ECMO circuit. The casing 60 is preferably transparent or translucent, and, like the cannula and propeller, should be nonthrombogenic, nonhemolytic, and bioinert. It is desirable to minimize the amount of contact between the propeller and the casing in order to minimize friction and heat. The propeller pitch should be relatively shallow to minimize turbulence.

Figure 8:
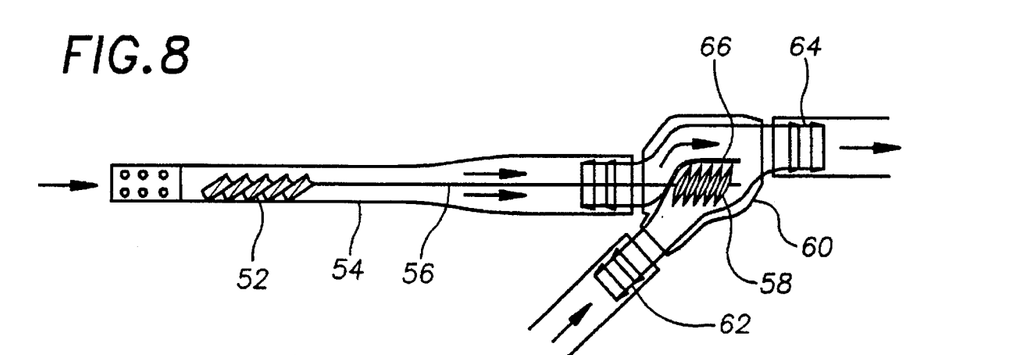
FIG. 8: An alternative active pumping cannula.
Figure 9:
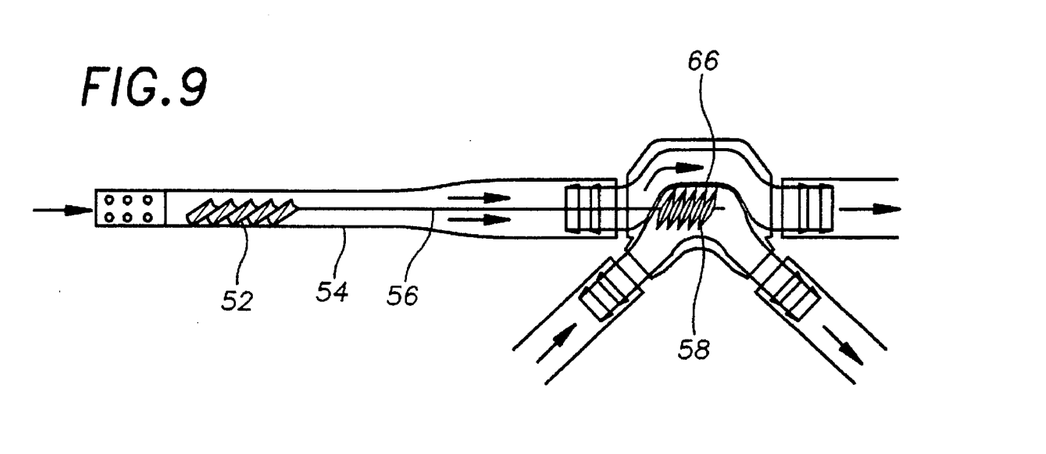
FIG. 9: An alternative active pumping cannula.

FIG. 8 shows a first alternative embodiment of an active pumping cannula, in which a divider 66 within the casing 60 separates bridge circuit flow over the helical driver 58 from venous blood flow through the cannula. FIG. 9 shows a second alternative embodiment in which rotation of the venous propeller is driven by the rotation of a helical driver 58 subjected to flow within a second segregated circuit. A divider 66 segregates the flows within the two circuits and the drive shaft 56 passes through a sealed aperture in the divider. Division of the flows allows the propeller to be driven by fluid flow from any available source.

Figure 10:
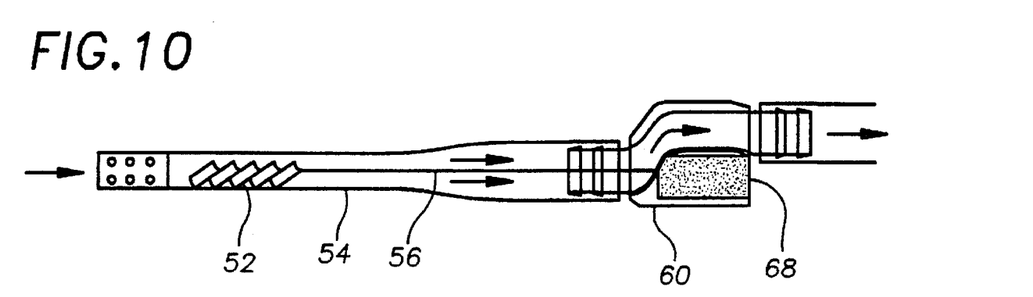
FIG. 10: An alternative active pumping cannula.
Figure 11:
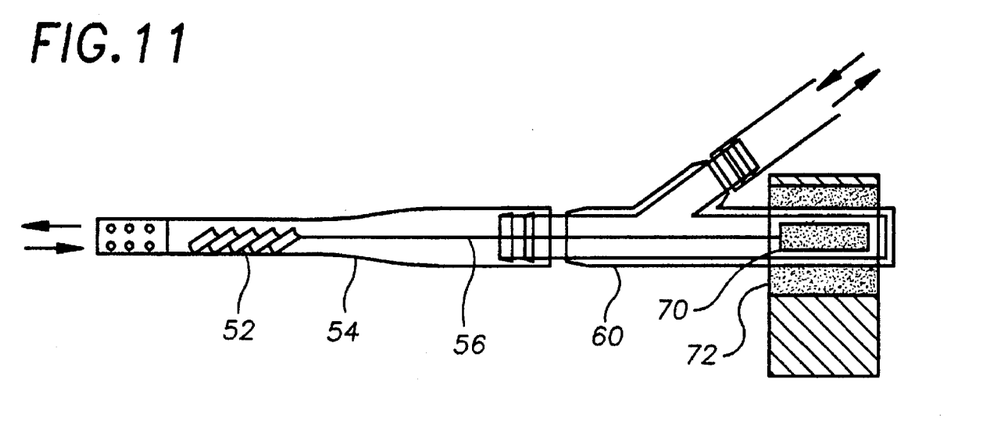
FIG. 11: An alternative active pumping cannula.

FIG. 10 shows a third alternative embodiment, in which continuous flow is actively maintained through the rotation of a motor driven helical propeller. The motor 68 is situated outside of the casing 60 and turns the propeller 52 by means of a drive shaft 56 which passes through a sealed aperture in the casing 60. FIG. 11 shows the preferred embodiment, in which the drive shaft 56 terminates in a cylindrical magnet 70 disposed within an aperture defined by the casing 60. An electrical coil 72 disposed about the magnet and external to the casing 60 imparts rotation to the magnet when electrical current is applied by means of electrical contacts (not shown).

Figure 12:
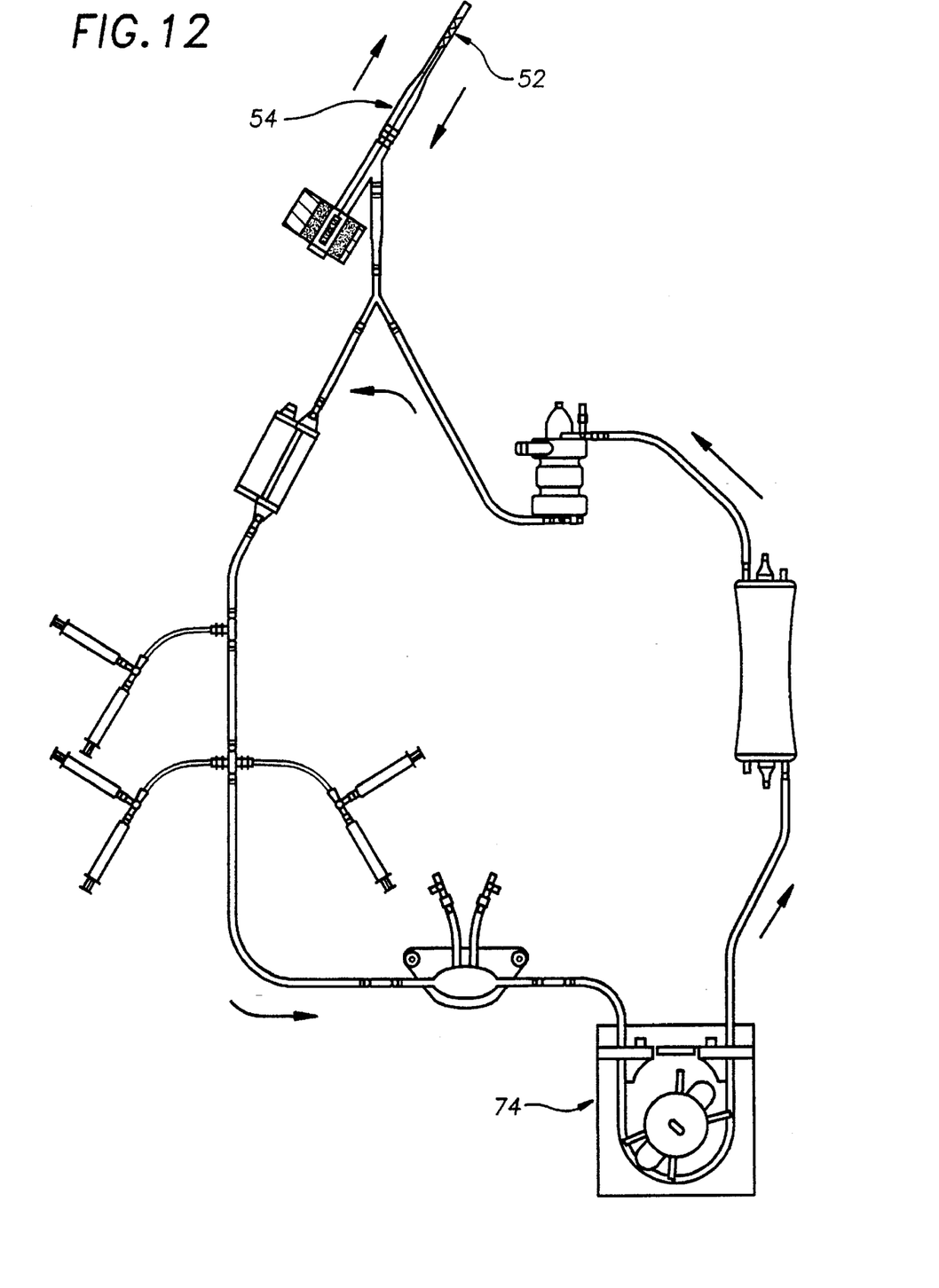
FIG. 12: A push/pull venovenous ECMO circuit incorporating the active pumping cannula of FIG. 11.

III. Bi-directional Helical Propeller as Fluid Propulsion Source in Single Lumen Push/Pull ECMO Apparatus Venovenous ECMO may be accomplished using a single lumen in a push/pull configuration. In the absence of flow assistance, the performance of these circuits is limited by the high input impedance which results from small lumen diameter. FIG. 12 shows a push/pull venovenous ECMO system which utilizes the active pumping cannula shown in FIG. 11 as a pumping unit used to overcome the input cannula impedance. The circuit utilizes a single cannula 54 for the dual purposes of alternately drawing venous blood into the circuit and emptying oxygenated blood back into the body. This is accomplished by first rotating the helical propeller 52 so as to draw blood from the subject into the venous cannula. From there, the blood will be drawn into the input branch of the ECMO circuit by the negative pressure caused by the primary pumping mechanism. Subsequently, the rotation of the propeller may be made passive to allow pressure from the roller pump to force oxygenated blood from the output branch of the ECMO circuit back through the cannula and into the subject. Alternately, the rotation of the helical propeller may be reversed, thereby assisting flow through the cannula and into the patient.

Bi-directional rotation is achieved by the application to the electrical coil 72 of an appropriate electrical current. The embodiment of the active pumping cannula shown in FIG. 10 could be analogously employed to perform the function described above.

IV. Bi-directional Helical Propeller as Fluid Propulsion Source in Single Lumen Tidal Liquid Ventilation Apparatus Liquid ventilation devices are a second type of device in which a liquid solution is circulated between an extracorporeal oxygenation circuit and a subject.

Figure 13:
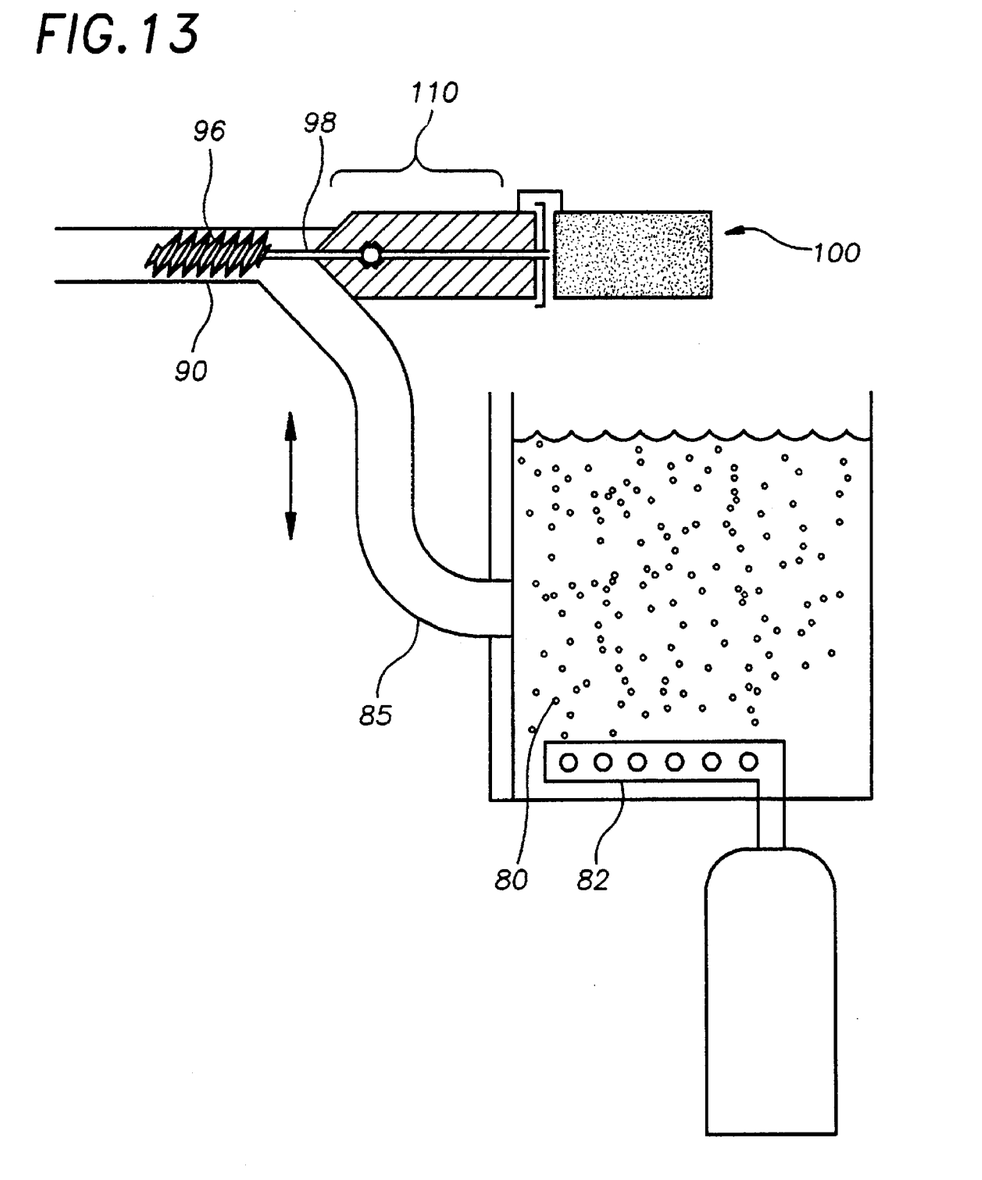
FIG. 13: A schematic diagram of a single reservoir, single conduit TLV circuit driven by a helical propeller.

FIG. 13 shows a schematic diagram of a single reservoir, single conduit TLV system which utilizes a helical propeller in accordance with the present invention. A liquid solvent contained in an oxygenation reservoir 80 is oxygenated by an oxygenator 82, such as a bubble oxygenator. A conduit 85 provides fluid communication between the oxygenation reservoir 80 and a propulsion unit 110 which acts as a pumping unit to propel solvent supplied from the oxygenation reservoir 80 through a propulsion tube 90 into an endotracheal tube (not shown) coupled thereto and thereby into a subject. The subsequently expired oxygen-depleted solvent flows from the patient through the propulsion tube 90 to the oxygenation reservoir 80 by means of the same conduit 85. In practice, the propulsion unit may be mounted on the side of the oxygenation reservoir.

Figure 14:
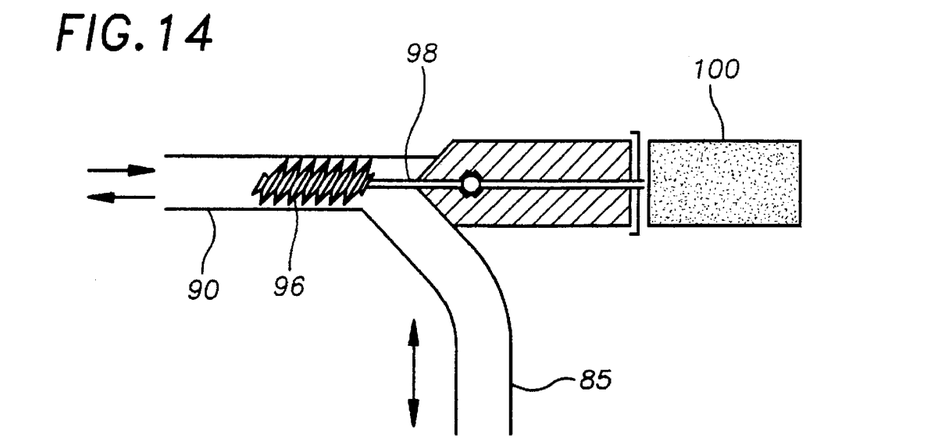
FIG. 14: A propulsion unit for a single conduit TLV circuit.

FIG. 14 shows the propulsion unit of the TLV system of FIG. 13. A helical propeller 96, rotated by a drive shaft 98, is contained within the propulsion tube 90. The drive shaft 98, coaxial with the propulsion tube 90, extends through a sealed aperture at the junction of the conduit 85 and the propulsion tube 90. The shaft 98 is turned by an electric motor 100 disposed externally to the propulsion unit. The propulsion tube and conduit of the propulsion unit are ideally transparent or translucent and impermeable to oxygen, and should be rigid and insoluble in the liquid solvent.

Figure 15:
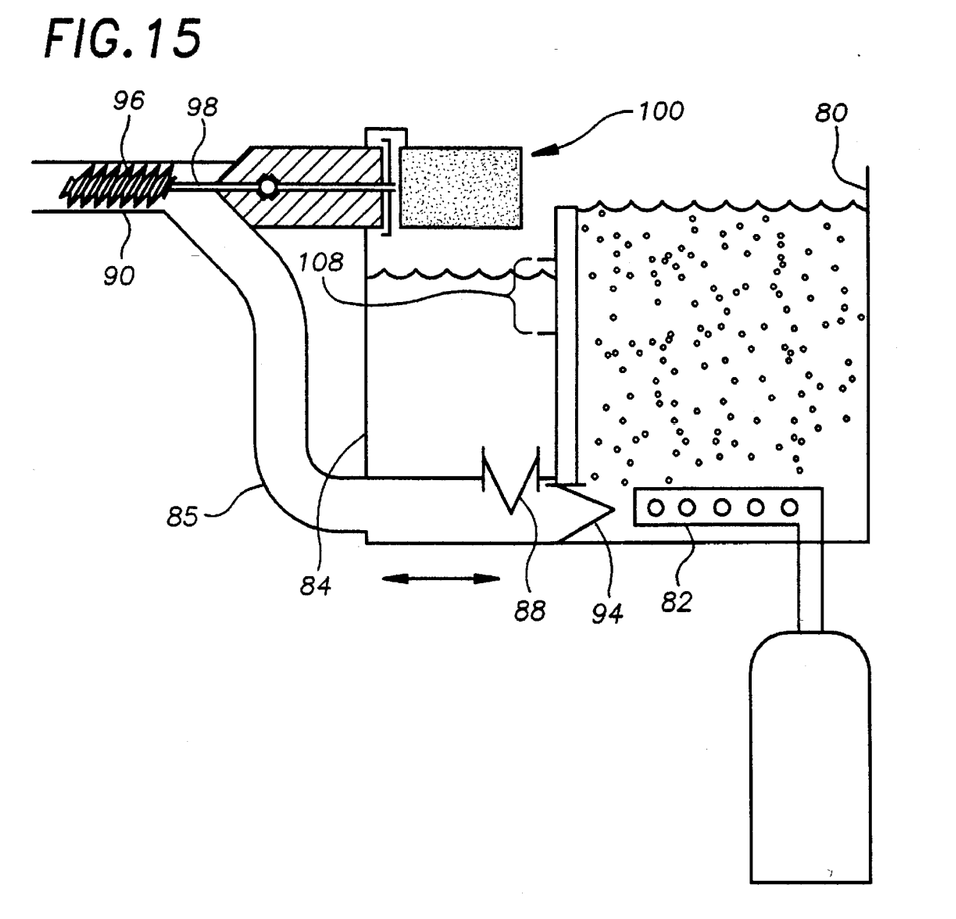
FIG. 15: A schematic diagram of a two reservoir, single conduit TLV circuit driven by a helical propeller.

FIG. 15 shows a schematic diagram of a two reservoir, single conduit TLV circuit which utilizes a helical propeller in accordance with the present invention. The circuit is comprised of an oxygenation reservoir 80 containing a liquid solvent which is oxygenated, for example, by a bubble oxygenator 82. A supply reservoir 84 receives oxygenated solvent from the oxygenation reservoir 80. Oxygenated solvent is supplied to a conduit 85 from the supply reservoir by means of a first unidirectional valve 88, such as a flap valve, ball and socket valve, tilt valve, or other well-known unidirectional valve. The conduit 85 conducts solvent to and from the propulsion tube 90 of a propulsion unit 110. The propulsion tube 90 may be coupled at its end, either directly or by means of other known intervening devices, to an endotracheal tube, by means of any of the coupling means which are well known in the art. Fluid is driven in alternating directions through the propulsion tube 90 by means of a rotating helical propeller 96 as previously described. A second unidirectional valve 94 allows oxygen-depleted solvent returning by means of the conduit to enter the oxygenation reservoir 80. Signal generating level fluid sensors 108 may be placed within the supply reservoir at positions which correspond to maximum allowable inspiratory and expiratory volumes.

Figure 16:
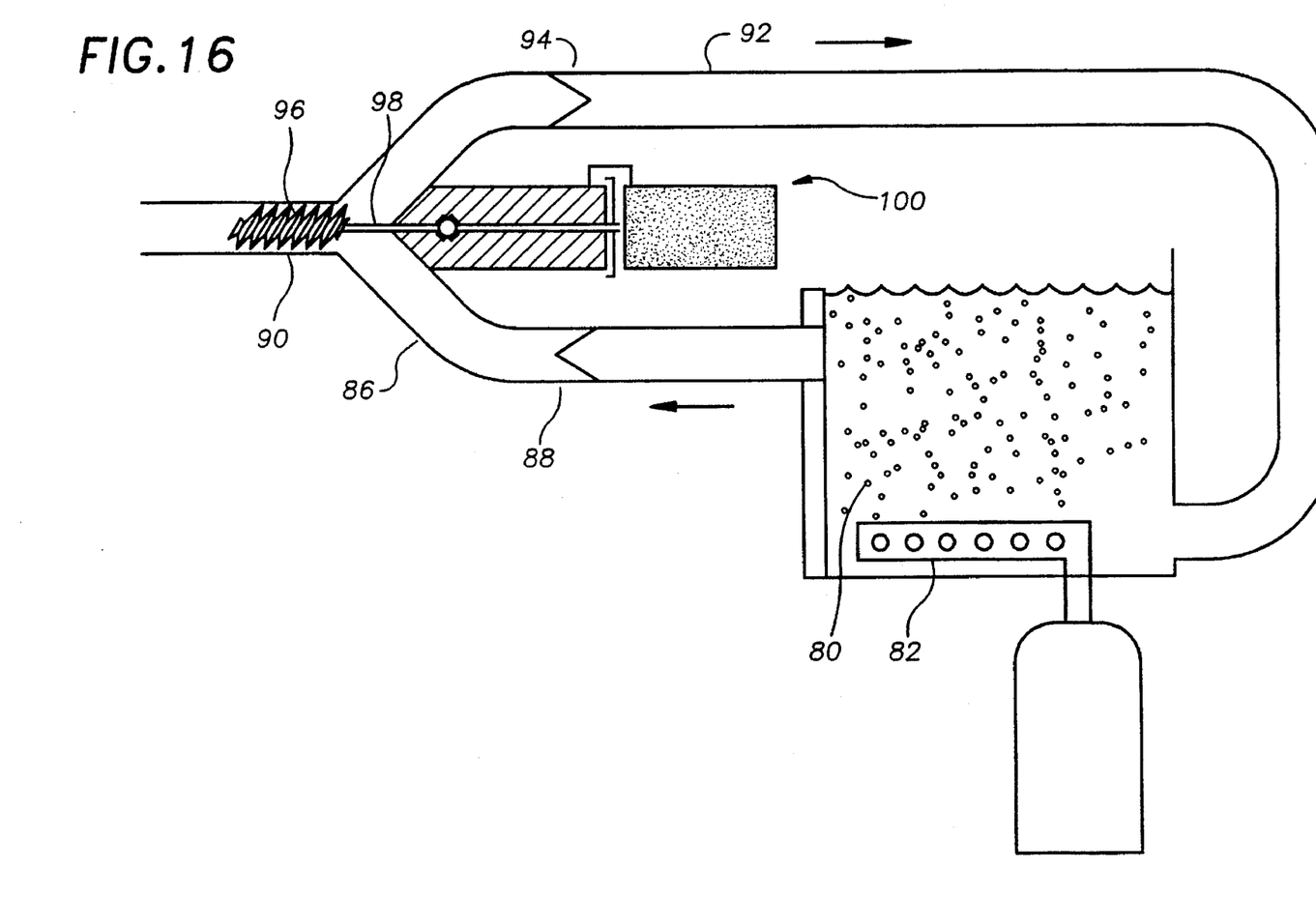
FIG. 16: A schematic diagram of a single reservoir, two conduit TLV circuit driven by a helical propeller.

FIG. 16 shows a schematic diagram of a single reservoir, two conduit TLV system which utilizes a helical propeller in accordance with the present invention. The circuit is comprised of an oxygenation reservoir 80 containing a liquid solvent which is oxygenated by an oxygenator 82, for example, a bubble oxygenator. A supply conduit 86 carries oxygenated solvent from the oxygenation reservoir 80 through a first unidirectional valve 88, such as a flap valve, ball and socket valve, tilt valve, or other well-known unidirectional valve, to a propulsion unit 110. The propulsion unit is comprised of a propulsion tube 90, which may be coupled at its end, either directly or by means of other known intervening devices, to an endotracheal tube, by means of any of the coupling means which are well known in the art. A return conduit 92 containing a second unidirectional valve 94 returns oxygen-depleted solvent from the propulsion tube 90 back to the oxygenation reservoir 80.

Figure 17:
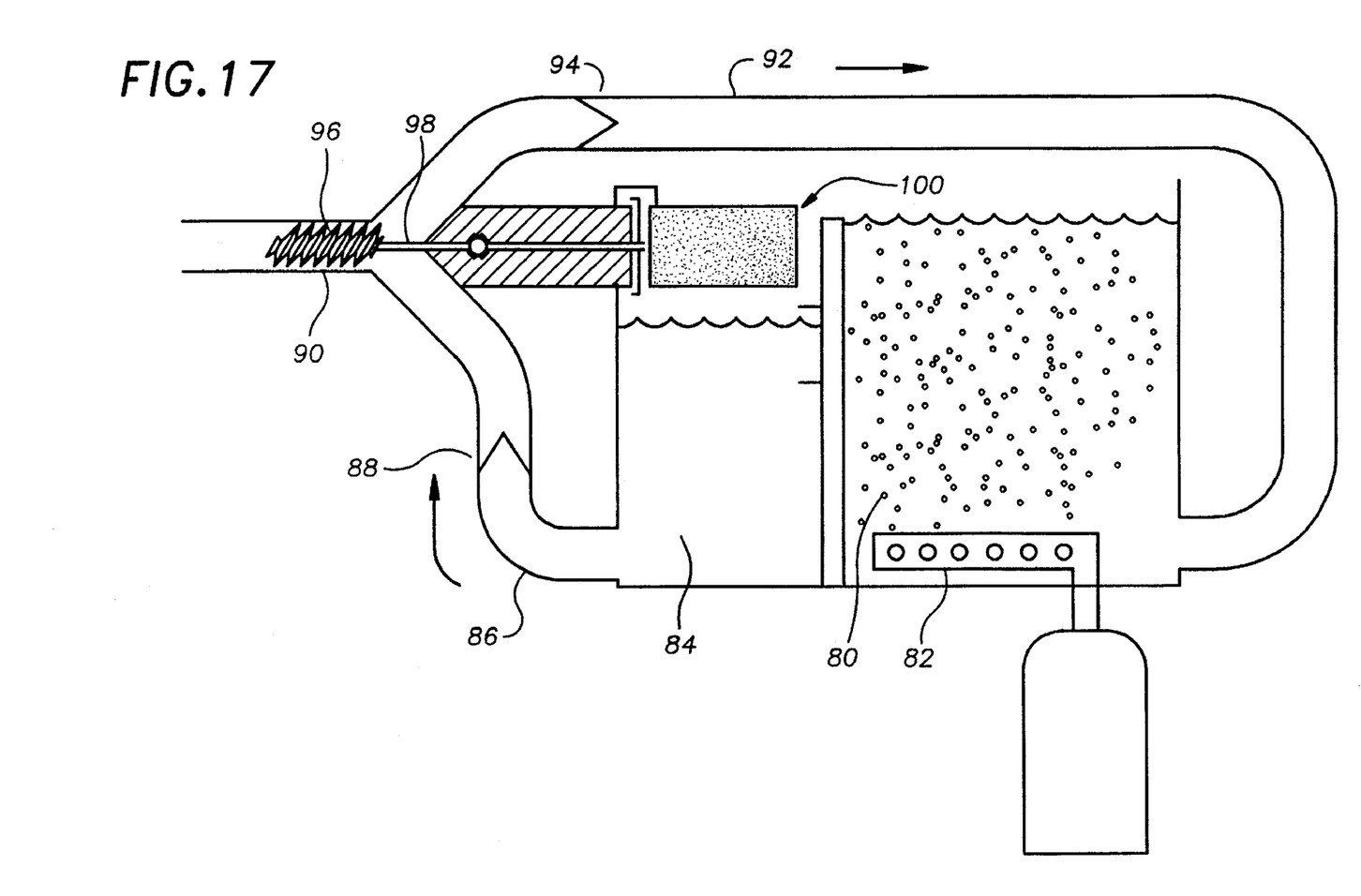
FIG. 17: A schematic diagram of a two reservoir, two conduit TLV circuit driven by a helical propeller.

FIG. 17 shows a schematic diagram of a two reservoir, two conduit TLV system which utilizes a helical propeller in accordance with the present invention. The circuit is comprised of an oxygenation reservoir 80 containing a liquid solvent which is oxygenated by an oxygenator 82, for example, a bubble oxygenator. A supply reservoir 84 holds oxygenated solvent and is fed by the oxygenation reservoir 80. A supply conduit 86 carries oxygenated solvent from the supply reservoir 80 through a first unidirectional valve 88, such as a flap valve, ball and socket valve, tilt valve, or other well-known unidirectional valve, to a propulsion unit 110. The propulsion unit is comprised of a propulsion tube 90, which may be coupled at its end, either directly or by means of other known intervening devices, to an endotracheal tube, by means of any of the coupling means which are well known in the art. A return conduit 92 containing a second unidirectional valve 94 returns oxygen-depleted solvent from the propulsion tube 90 back to the oxygenation reservoir 80.

Figure 18:
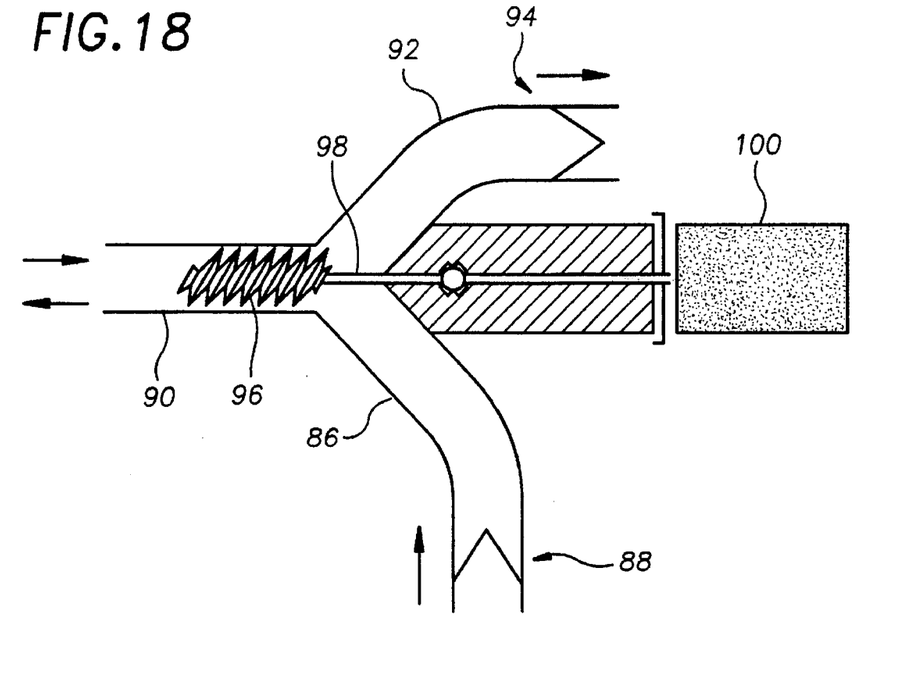
FIG. 18: A first alternative two conduit TLV propulsion unit.
Figure 19:
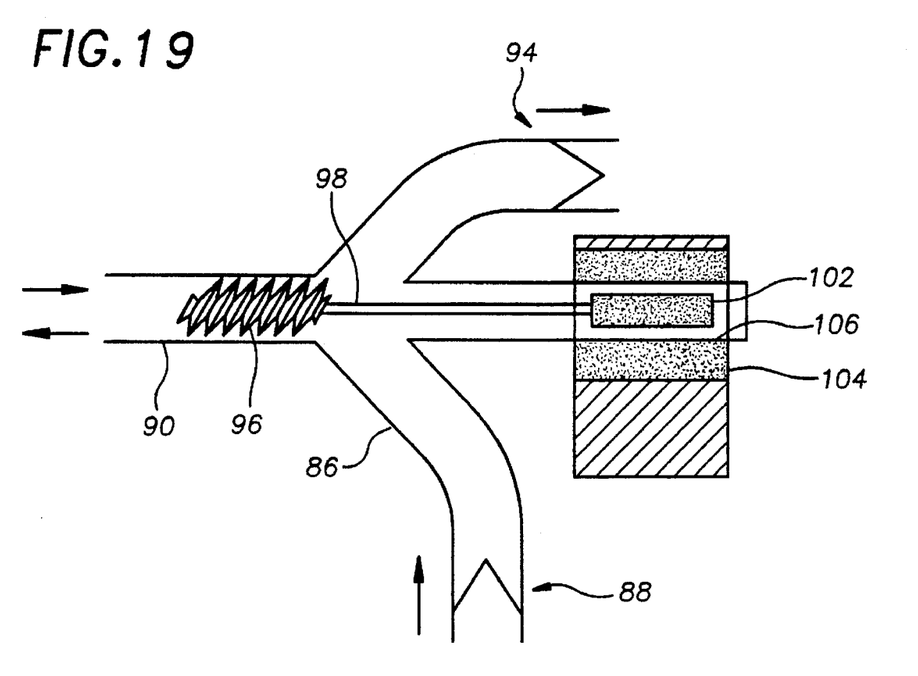
FIG. 19: A second alternative two conduit TLV propulsion unit.

FIG. 18 shows the propulsion unit of the TLV systems of FIGS. 16 and 17. A helical propeller 96, rotated by a drive shaft 98, is contained within a propulsion tube 90. A drive shaft 98, coaxial with the propulsion tube 90, extends through a sealed aperture at the junction of the supply conduit 86 and the return conduit propulsion tube 90. The shaft 98 is turned by an electric motor 100 disposed externally to the propulsion unit. FIG. 19 shows an alternative preferred propulsion unit, in which the drive shaft 98 terminates in a cylindrical magnet 102 which is aligned coaxially with the drive shaft 98 and contained within a closed conduit 106. An electrical coil 104 disposed about the magnet 102 and external to the conduit 106 provides a means for turning the magnet and drive shaft. The magnet and coil embodiment of the propulsion unit may be adapted for use with any of the alternative TLV propulsion units disclosed herein.

In operation, the propulsion unit provides repetitive cycles of inhalation and expiration. During the period of inspiration, the helical propeller rotates for a time in the axial direction appropriate for propelling solvent through the propulsion tube and endotracheal tube and into the patient. During the period of expiration, the helical propeller rotates for a time in the opposite direction, causing solvent to flow back from the endotracheal tube through the propulsion unit and into the oxygenation reservoir. Alternately, during the period of expiration, propeller rotation may be made passive to allow the recoil of the lungs to propel solvent back through the propulsion unit.

An advantage of the use of the helical propeller as a propulsion source in liquid breathing is that the axial fluid pressure waveform generated by the helical propeller is proportional to the waveform over time of the rate of rotation of the propeller. For example, a respiratory rate of 6 breaths per minute can be achieved by alternating the rotation direction of the propeller at a frequency of 6 cycles per minute. This attribute makes conceivable the construction of advanced devices in which the pressure waveform may be customized in accordance with particular therapeutic purposes. For example, inspiration and expiration periods could be made asymmetrical, or flow rates at certain points in the respiratory cycle could be manipulated to simulate the effects of natural functions such as coughing.

Another advantage of the use of helical propellers is that they allow slip in instances where end-expiratory pressure differences exist between the trachea and the liquid breathing circuit. This may be applied therapeutically, for instance, to preserve the functional residual capacity of the lungs.

Other elements could conceivably be added to such a liquid breathing apparatus, including a heater/cooler to maintain proper solvent temperature, flow probes to monitor inspiratory and expiratory flow rates and volumes, circuitry for limiting the maximum inspiratory and expiratory volumes, and pressure transducers to ascertain airway pressures.

We claim:

1. An ECMO system comprising:
   a membrane oxygenator for oxygenating blood provided to the system;
   first conduit means for providing fluid communication between a circulatory system of a subject and an input of said membrane oxygenator;
   second conduit means for providing fluid communication between an output of said membrane oxygenator and said circulatory system of said subject;
   first pump means comprising a helical propeller disposed within said first conduit means for propelling blood toward said input of said membrane oxygenator; and
   second pump means comprising a helical propeller disposed within said second conduit means for propelling blood away from said output of said membrane oxygenator.

2. The apparatus of claim 1, wherein said second conduit means comprises a compliant membrane disposed between said output of said membrane oxygenator and said second pump means.

3. The apparatus of claim 1, further comprising third conduit means for conducting fluid from an output of said pumping means to an input of said venous cannula, said third conduit means comprising a flow regulator for regulating flow of fluid through said third conduit means.

4. A tidal liquid ventilation apparatus comprising:
   containment means for containing a quantity of liquid ventilation solution;
   conduit means in fluid communication with said containment means for conducting solution to and from said containment means;
   a propulsion unit in fluid communication with said conduit means, said propulsion unit comprising:
      a propulsion tube for transporting said liquid ventilation solution between a subject receiving liquid ventilation and said conduit means;
      a helical propeller disposed within the lumen of said propulsion tube for propelling liquid ventilation solution disposed within said propulsion tube;
      propeller rotation means for imparting axial rotation to said helical propeller; and
   means for periodically rotating said helical propeller to propel a quantity of liquid ventilation fluid from said containment means through said propulsion tube.

5. The apparatus of claim 1, further comprising means for periodically rotating said helical propeller to propel a quantity of liquid ventilation fluid to said containment means through said propulsion tube.

6. The apparatus of claim 4, wherein said propeller rotation means is capable of imparting rotation to said propeller in either direction of axial rotation.

7. The apparatus of claim 4, wherein said propulsion tube is in fluid communication with said subject by means of an endotracheal tube.

8. The apparatus of claim 4, wherein said conduit means comprises:
   a supply conduit for transporting liquid ventilation solution from said containment means to said propulsion unit; and,
   a return conduit for transporting liquid ventilation solution from said propulsion unit to said containment means.

9. The apparatus of claim 8, wherein said containment means comprises an oxygenation reservoir and a supply reservoir, and said conduit means further comprises:
   a first unidirectional valve for preventing flow within said supply conduit from said propulsion unit to said supply reservoir; and,
   a second unidirectional valve for preventing flow within said return conduit from said oxygenation reservoir to said propulsion unit.

10. The apparatus of claim 4, wherein said containment means comprises an oxygenation reservoir and a supply reservoir.

11. The apparatus of claim 10, wherein said conduit means comprises:
   a supply conduit for transporting liquid ventilation solution from said containment means to said propulsion unit; and,
   a return conduit for transporting liquid ventilation solution from said propulsion unit to said containment means.

12. The apparatus of claim 11, further comprising:
   a first unidirectional valve for preventing flow within said supply conduit from said propulsion unit to said supply reservoir; and,
   a second unidirectional valve for preventing flow within said return conduit from said oxygenation reservoir to said propulsion unit.

13. The apparatus of claim 4, wherein said containment means comprises an oxygenation reservoir and a supply reservoir, and said conduit means further comprises:

a first unidirectional valve for preventing flow within said conduit means from said propulsion unit to said supply reservoir; and, a second unidirectional valve for preventing flow within said conduit means from said oxygenation reservoir to said propulsion unit.

14. An ECMO system comprising:

a membrane oxygenator for oxygenating blood provided to the system;

first conduit means for conducting fluid received from a circulatory system of a subject to an input of said membrane oxygenator;

second conduit means for providing fluid communication between an output of said membrane oxygenator and said circulatory system of said subject;

pumping means for driving fluid within said system from said first conduit means through said membrane oxygenator to said second conduit means;

a venous cannula for providing fluid communication between said circulatory system of said subject and said first conduit means, said venous cannula comprising a helical propeller disposed within the lumen of said cannula and means for rotating said helical propeller to propel blood through said cannula from said subject to said first conduit means.

15. A venovenous ECMO system comprising:

a membrane oxygenator for oxygenating blood provided to the system;

first conduit means for conducting blood to an input of said membrane oxygenator;

second conduit means for conducting blood from an output of said membrane oxygenator;

pumping means for driving fluid within said system from said first conduit means through said membrane oxygenator to said second conduit means;

a venous cannula for providing fluid communication between said circulatory system of said subject and said first conduit means;

a helical propeller disposed within the lumen of said venous cannula; and means for alternately rotating said helical propeller in a first direction to propel blood through said venous cannula from said subject to said first conduit means and in a second direction to propel blood through said venous cannula from said second conduit means to said subject.

* * * * *